United States Patent [19]

Wiech et al.

[11] 4,310,524

[45] Jan. 12, 1982

[54] TCA COMPOSITION AND METHOD FOR RAPID ONSET ANTIDEPRESSANT THERAPY

[75] Inventors: Norbert L. Wiech; Richard C. Ursillo, both of Cincinnati, Ohio

[73] Assignee: Richardson-Merrell, Inc., Wilton, Conn.

[21] Appl. No.: 139,498

[22] Filed: Apr. 11, 1980

[51] Int. Cl.$^3$ .................... A61K 31/33; A61K 31/135
[52] U.S. Cl. ...................................... 424/244; 424/330
[58] Field of Search ................................ 424/244, 330

[56] References Cited

PUBLICATIONS

Chemical Abst., vol. 66-72828m, (1967), Kellett.
Chemical Abst., vol. 68-94371a, (1968), Martelli et al.
Chemical Abst., vol. 74-86048j, (1971), Dixit et al.
Holmberg et al., *Psychopharm.*, 2, 93 (1961).
Svensson, *Symp. Med. Hoechst.*, 13, 245 (1978).
McMillen et al., *Fed. Proc.*, 38, 592 (1979).
Sellinger et al., *Fed. Proc.*, 38, 592 (1979).
Pandey et al., *Fed. Proc.*, 38, 592 (1979).

*Primary Examiner*—Stanley J. Friedman
*Attorney, Agent, or Firm*—Millen & White

[57] ABSTRACT

A method is provided for treating depression in a patient therefrom and requiring rapid symptomatic relief, which comprises administering to said patient concurrently (a) an effective antidepressant amount of a tricyclic antidepressant or a pharmaceutically effective acid addition salt thereof, and (b) an amount of an α-adrenergic receptor blocking agent effective to achieve rapid onset of the antidepressant action of (a), whereby the onset of said antidepressant action is achieved within from 1 to 7 days.

A pharmaceutical composition is also provided which is especially adapted for use with the foregoing method.

17 Claims, No Drawings

TCA COMPOSITION AND METHOD FOR RAPID ONSET ANTIDEPRESSANT THERAPY

BACKGROUND OF THE INVENTION

This invention relates to a method for acclerating the rate of onset of antidepressant action of clinically effective tricyclic antidepressants (TCA's) by combining them with synergistic α-adrenergic receptor blocking agents (α-blockers). The invention also relates to a pharmaceutical composition suitable for use with the foregoing method.

The use of tricyclic antidepressants is well known. One of the disadvantages of these agents is that the onset of antidepressant therapeutic activity is slow, often requiring several weeks before a satisfactory effect is achieved. In cases of severe depression, where suicide is a serious risk, a rapid onset of antidepressant activity is highly desirable.

More recently, combinations of tricyclic antidepressants and phenothiazines or butyrophenone antipsychotic agents have been used to substantially accelerate the onset of antidepressant activity. The present inventors are not aware of any reports of clinical use of the TCA/α-blocker combinations of this invention in antidepressant therapy.

Holmberg et al., in Psychopharm., 2, 93(1961), reported a study of how the TCA imipramine modified the effects of the α-blocker yohimbine in 7 subjects (4 schizophrenics, 1 alcoholic and 2 psychopaths). No depressives were studied using the combination.

Svensson, in a symposium on Depressive Disorders, May 9-11, 1977, published in Symp. Med. Hoechst, 13, 245-254 (Schattauer, Stuttgart and New York, 1978), suggested the theoretical possibility of enhancing the effect of tricyclic antidepressants especially secondary amine types such as desipramine, with yohimbine. In the single experiment reported, the firing rate of a noradrenergic cell in the locus coereleus of a rat was inhibited by desipramine and the inhibition was then antagonized by a more than three-fold excess of yohimbine.

Animal studies of the effects of the α-blockers dibozane and prazosin on rats fed rather high chronic doses of desipramine were reported by McMillen et al., Fed. Proc., 38, 592 (1979).

Attempts to correlate α-receptor effects or firing rates of norepinephrine neurons in the locus coereleus with both the chemical intensity and temporal activity profiles of antidepressants has been less than successful.

However, recent research has shown that the antidepressant activity of a wide variety of antidepressant drugs as well as of chronic electroshock is well correlated with a β-receptor assay in an animal model. Specifically, the temporal profile of the onset of antidepressant activity in humans closely parallels the decrease in β-adrenergic receptor density in rat cerebrocortical tissue, as determined by a measurement of the binding of tritiated dihydroalprenolol ($^3$H-DHA) using liquid scintillation spectrometry. Thus, this method of assay of antidepressant drugs in rats by its capability to decrease brain β-adrenergic receptors using the ligand $^3$H-DHA is far superior to any previously described method, since the effect is common to all known antidepressants and measures the time of onset of the antidepressant activity as well.

SUMMARY OF THE INVENTION

In a method aspect, the present invention provides a method for treating depression in a patient suffering therefrom, and requiring rapid symptomatic relief, which comprises administering to said patient concurrently (a) an effective antidepressant amount of a tricyclic antidepressant or a pharmaceutically effective acid addition salt thereof, and (b) an amount of an α-adrenergic receptor blocking agent effective to achieve rapid onset of the antidepressant action of (a); whereby the onset of said antidepressant action is achieved within from 1 to 7 days.

In a composition aspect, the present invention provides an antidepressant composition which is suitable for use with the above method.

DETAILED DESCRIPTION OF THE INVENTION

The tricyclic antidepressants used in the method of the invention are defined pharmacologically by their ability to significantly lower β-adrenergic receptor density in rat cerebrocortical tissue after prolonged/chronic administration, whereas single or short-term administration fails to achieve significant β-receptor lowering. The broad scope of this class of antidepressants is described in Fielding et al., Eds., *"Industrial Pharmacology, Vol. II, Antidepressants,"* pages 3-43 (Futura Publishing Co., Inc., Mount Kisco, N.Y., 1975).

Prominent among the tricyclic antidepressants are the linear tricyclics, e.g., imipramine, desipramine, amitriptyline, nortriptyline, protriptyline, doxepin, ketipramine, mianserin, dothiepin, amoxapine, dibenzepin, melitracen, maprotiline, flupentixol, azaphen, and related compounds showing similar activity. Angular tricyclics include indriline, clodazone, nomifensin, and related compounds. A variety of other structurally diverse antidepressants, e.g., iprindole, wellbatrin, nialamide, phenelzine and tranylcypromine have been shown to produce β-receptor subsensitivity upon chronic administration, as reported by Sellinger et al. and Pandey et al. In *Fed. Proc.*, 38, 592 (1979). They are functionally equivalent to the tricyclic antidepressants and are therefore included within the scope of the invention. Thus, the term tricyclic antidepressant is intended by the present inventors to embrace the broad class of antidepressants described above together with related compounds sharing the common property that they all depress cerebrocortical β-adrenergic receptor density on chronic administration.

The α-adrenergic receptor blocking agents of this invention include: yohimbine, piperoxan, mianserin and metiamide which are primarily $α_2$-blockers; prazosin, thymoxamine, dibozane and clozapine which are primarily $α_1$-blockers; and phentolamine and phenoxybenzamine which have substantially equal blocking effects on $α_1$-receptors and $α_2$-receptors, or pharmaceutically acceptable acid addition salts thereof. Contemplated equivalents include other α-blockers which are structurally and/or pharmacologically related to the foregoing, e.g., corynanthine which is a stereoisomer of yohimbine and has similar pharmacological properties, tolazoline which is an analog of phentolamine and has similar uses, and dibenamine which is structurally and pharmacologically related to phenoxybenzamine.

Drugs are classified as $α_1$-blockers and/or $α_2$ blockers according to their ability to inhibit different effects of norepinephrine, as reviewed by Starke, "Regulation of Norepinephrine Release by Presynaptic Receptor Systems," *Rev. Physiol. Biochem. & Pharmacol.*, 77, 1 (1977).

The tricyclic antidepressant and/or the α-blocker may be administered in the form of a pharmaceutically acceptable acid addition salt, e.g., salts with inorganic acids such as, for example, hydrochloric, hydrobromic, sulphuric, phosphoric acids and the like and with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic acid and the like. The salts may be prepared by adding an organic or mineral acid to a solution of the free base in an organic solvent, and further purified by chromotography and/or recrystallization.

The tricyclic antidepressants imipramine, desipramine, amitriptyline, nortriptyline, and doxepin are available commercially, and their syntheses are well known to those skilled in the art. Related tricyclic antidepressants are accessible by analogous synthetic pathways. The α-blockers are likewise either available commercially or by well known synthetic pathways.

One of the disadvantages of the tricyclic antidepressants is that, used alone, their onset of activity is slow, requiring several weeks before an acceptable level of antidepressant activity is shown. In cases of severe depression, where suicide is a serious risk, this slow onset of activity can be a great handicap. Increasing the dosage will accelerate the decrease in β-receptor density and the onset of antidepressant activity, but toxic side effects are produced which militate against such dosage levels.

In accordance with this invention, surprisingly the administration of a combination of a relatively low, non-toxic dose of a tricyclic anti-depressant and an α-blocker will accelerate the onset of antidepressant activity such that a clinical reversal of the depressive state will be achieved within from 1 to 7 days.

While not wishing to be bound by a particular mechanism, it appears that the onset of antidepressant activity is due to a decrease in β-adrenergic receptor density and is accompanied by $\alpha_2$-receptor subsensitization, resulting in a higher synaptic concentration of norepinephrine and increased postsynaptic $\beta_1$-receptor stimulation. An effective antidepressant combination thus appears to act by stimulating an increase in norepinephrine release while inhibiting the feedback mechanism which attempts to compensate by an increase in norepinephrine uptake.

It has been found experimentally that daily intraperitoneal administration of 5 mg/kg of desipramine does not appreciably lower the density of β-adrenergic receptors in rat cerebrocortical tissue, as determined by the binding of $^3$H-DHA in the model described hereinabove, after administration for 28 consecutive days. Significant reduction in β-adrenergic receptor density can be achieved with 42 days of chronic desipramine treatment. This closely parallels the time of development of antidepressant activity in human patients. The co-administration of desipramine with the α-blockers yohimbine or prazosin for 4 days at a dosage level of 5 mg/kg once daily of desipramine and 2 mg/kg twice daily of yohimbine or 5 mg/kg twice daily of prazosin, produces a marked reduction of β-adrenergic receptor density. The criticality of the dosage levels is shown by the fact that administration of 1 mg/kg twice daily of yohimbine instead of 2 mg/kg in the foregoing experiment resulted in only a marginal reduction of β-adrenergic receptor density.

In the method for treating depression of the present invention, a dosage level of from 0.1 to 5 mg/kg of body weight of the patient per day of the tricyclic antidepressant is combined with a dosage of from 0.1 to 10 mg/kg of patient body weight per day of α-blocker, or a pharmaceutically acceptable acid addition salt of one or both of the foregoing. Preferably, the combination is administered three times daily in equal dosages. Preferred dosages ranges for the tricyclic antidepressants and representative α-blockers are shown in Table 1.

TABLE 1

| Compound | Preferred Dose Range-mg/kg/day |
|---|---|
| Tricyclic antidepressant | 1.5–4.0 |
| α-blocker | |
| Yohimbine | 0.2–1.0 |
| Piperoxan, phentolamine, prazosin, phenoxybenzamine | 0.5–2.0 |
| Mianserin, dibozane, thymoxamine | 1.0–4.0 |
| Clozapine | 2.0–6.0 |
| Metiamide | 5.0–10.0 |

Preferred and especially preferred ratios of TCA to representative α-blockers in the method and composition of the invention are given in Table 2 (wt. TCA/wt. α-blocker).

TABLE 2

| Combination | Prefd. wt. ratio | Esp. Prefd. wt. ratio |
|---|---|---|
| TCA/yohimbine | 10–40 | 15–25 |
| TCA/phentolamine | 1–10 | 2–4 |
| TCA/prazosin | 2–50 | 5–20 |
| TCA/phenoxybenzamine or piperoxan or dibozane or thymoxamine | 2–40 | 3–10 |
| TCA/clozapine | 0.2–4 | 0.5–1 |
| TCA/metiamide | 0.15–1 | 0.2–0.3 |
| TCA/mianserin | 0.3–6 | 1–2 |

The method of the present invention may be effected with either oral or parenteral administration of the drugs, in solid or liquid form, and in the presence of a pharmaceutically acceptable carrier if desired. Solid dosage unit forms, e.g., capsules, pills, tablets and the like are suitable for administration of the combination of drugs. Individual solid dosage units may contain, in addition to the active ingredients, a pharmaceutically acceptable carrier, e.g., starch, sugar, sorbitol, gelatin, lubricants, silicic acid, talcum, and the like. Alternatively, liquid dosage forms for either oral administration or sterile injectible solutions are suitable for used with the present method. More than one form of administration may be use where such is found to be clinically useful. For example, the first few administrations may be by injection, and subsequent treatment continued using capsules or tablets once the patient's condition is sufficiently improved. Examples of suitable dosage forms are given hereinbelow, although the invention is not limited in any way by the examples chosen, since these modes of administration are generally known to the art.

Administration of the combination is desirably effected in from 1 to 4 portions daily, preferably by oral administration, e.g., capsules or tablets, thrice daily, e.g., with meals. Each dosage unit will contain from about 1 to about 750 mg, preferably from about 20 to about 500 mg, and most preferably from about 40 to about 100 mg of the tricyclic antidepressant or a pharmaceutically aceptable acid addition salt thereof, and from about 1 to about 2000 mg of the α-blocker or a pharmaceutically acceptable addition salt thereof. Preferred amounts of the α-blockers are readily determined from the preferred ratios of TCA/α-blockers in Table 2 hereinabove.

Preferred dialy dosage ranges for the antidepressants are shown in Table 3.

TABLE 3

| Antidepressant | Normal daily dosage (mg) | Recommended maximum dose (mg) |
|---|---|---|
| Imipramine | 100–200 | 300 |
| Desipramine | 100–200 | 300 |
| Doxepin | 75–150 | 300 |
| Amitriptyline | 100–200 | 300 |
| Nortriptyline | 75–100 | 100 |
| Protriptyline | 15–40 | 60 |
| Iprindole | 100–200 | 300 |
| Mianserin | 100–200 | 300 |
| Tranylcypromine | 100–200 | 300 |

The following examples are illustrative but not limitative of the method and the composition of the present invention. Other suitable modifications and adaptations to the variety of conditions and parameters normally encountered in clinical antidepressant therapy and which are obvious to those skilled in the art are within the spirit and scope of this invention.

EXAMPLE 1

Tablet Formulation

An illustrative tablet formulation suitable for use in making up the antidepressant composition of the invention and suitable for use in the method for treating depression of the invention is as follows. The proportions are designed for administration to a patient weighing about 80 kg in a regimen wherein administration is thrice daily.

| (a) Desipramine hydrochloride | 50 g |
|---|---|
| (b) Yohimbine hydrochloride | 10 g |
| (c) Wheat starch | 7 g |
| (d) Lactose | 20 g |
| (e) Magnesium stearate | 1 g |

A granulation obtained upon mixing the lactose with a portion of the starch and a granulated starch paste made from the remainder of the strach is dried, screened, and mixed with the active ingredients (a) and (b) and the magnesium stearate. The mixture is compressed into 1000 tablets each weighing 88 mg.

Analogously, an equal weight of imipramine, doxepin, amitriptyline nortriptyline or protriptyline may be substituted for desipramine to produce tablets according to the invention.

Substitution of 25 g of phentolamine, 8 g of prazosin, 10 g of one of piperoxan, phenoxybenzamine, dibozane or thymoxamine, 40 g of mianserin, 70 g o clozapine or 200 g of metiamide, or a pharmaceutically acceptable acid addition salt thereof, for the 10 g of yohimbine hydrochloride in any of the foregoing, with a proportional adjustment of the amounts of (c)–(e) will result in tablets according to the invention.

EXAMPLE 2

Pill Formulation

Pills illustrative of the composition of the invention, and suitable for use in the method of the invention may be prepared as follows. As in Example 1, the pill formulation is designed for administration to a patient weighing about 80 kg, and designed for thrice daily administration.

|  | Per Pill |
|---|---|
| (a) Imipramine hydrochloride | 100 mg |
| (b) Phenoxybenzamine hydrochloride | 30 mg |
| (c) Corn starch | 85 mg |
| (d) Liquid glucose | 13 ml |

The pills are prepared by blending the active ingredients (a) and (b) and the corn starch, then adding the liquid glucose with thorough kneading to form a plastic mass from which the pills are cut and formed.

Analogously to Example 1, other TCA's and α-blockers may be substituted to produce analogous pills according to the invention.

EXAMPLE 3

Gelatin Capsule Formulation

Hard gelatin capsules illustrative of the composition of the invention, and suitable for use in the method for treating depression of the invention are prepared as follows. Each dosage unit is designed for administration to a patient weighing about 80 kg, and thrice daily administration is envisioned.

|  | Per Capsule |
|---|---|
| (a) Amitriptyline hydrochloride | 75 mg |
| (b) Clozapine hydrochloride | 50 mg |
| (c) talc | 20 mg |

A capsule is prepared by passing dry powdered active ingredients (a) and (b) and powdered talc in the above proportions through a fine mesh screen and mixing them well. The powder is then filled into No. 0 hard gelatin capsules at a net fill of 145 mg per capsule.

Analogous capsules are prepared analogously to the above, using proportional amounts of other TCA's and-/or α-blockers as shown in Example 1.

We claim:

1. In a method for treating depression by administering to a patient suffering therefrom an effective antidepressant amount of imipramine or desipramine or a pharmaceutically acceptable acid addition salt thereof, the improvement which comprises accelerating the onset of antidepressant action of said antidepressant by concurrently administering to said patient an α-adrenergic receptor blocking agent, said blocking agent being yohimbine, piperoxan, prazosin, phentolamine, metiamide, phenoxybenzamine, thymoxamine, dibozane, clozapine, or mianserin, or a pharmaceutically acceptable acid addition salt thereof; wherein said blocking agent is administered in an amount effective to achieve the onset of said antidepressant activity within from 1 to 7 days.

2. The method of claim 1, wherein the α-adrenergic blocking agent is yohimbine or a pharmaceutically acceptable acid addition salt thereof.

3. The method of claim 1, wherein the α-adrenergic blocking agent is prazosin, piperoxan, phentolamine or phenoxybenzamine or a pharmaceutically acceptable acid addition salt thereof.

4. The method of claim 1, wherein the α-adrenergic blocking agent is mianserin, thymoxamine or dibozane or a pharmaceutically acceptable acid addition salt thereof.

5. The method of claim 1, wherein the α-adrenergic blocking agent is clozapine or a pharmaceutically acceptable acid addition salt thereof.

6. The method of claim 1, wherein the α-adrenergic blocking agent is metiamide or a pharmaceutically acceptable acid addition salt thereof.

7. The method of claim 1, wherein the amount of the antidepressant or pharmaceutically acceptable acid addition salt thereof is from 0.1 to 5 mg per kg of patient body weight per day, and the amount of the α-adrenergic blocking agent or pharmaceutically acceptable acid addition salt thereof is from 0.1 to 10 mg per kg of patient body weight per day.

8. The method of claim 1, wherein the amount of the antidepressant or pharmaceutically acceptable acid addition salt thereof is from 1.5 to 4.0 mg per kg of patient body weight per day.

9. The method of claim 2, wherein the amount of yohimbine or a pharamaceutically acceptable acid addition salt thereof is from 0.2 to 1.0 mg per kg of patient body weight per day.

10. The method of claim 3, wherein the amount of piperoxane, phentolamine, prazosin or phenoxybenzamine or a pharmaceutically acceptable acid addition salt thereof is from 0.5 to 2.0 mg per kg of patient body weight per day.

11. The method of claim 6, wherein the amount of mianserin, thymoxamine or dibozane or a pharmaceutically acceptable acid addition salt thereof is from 1.0 to 4.0 mg per kg of patient body weight per day.

12. The method of claim 5, wherein the amount of clozapine or a pharmaceutically acceptable acid addition salt thereof is from 2.0 to 6.0 mg per kg of patient body weight per day.

13. The method of claim 6, wherein the amount of metiamide or a pharmaceutically acceptable acid addition salt thereof is from 5.0 to 10.0 mg per kg of patient body weight per day.

14. The method of claim 9, wherein the antidepressant is desipramine in an amount of from 1.5 to 4.0 mg per kg of patient body weight per day.

15. The method of claim 10, wherein the antidepressant is desipramine in an amount of from 1.5 to 4.0 mg per kg of patient body weight per day.

16. The method of claim 15, wherein the α-adrenergic blocking agent is prazosin or a pharmaceutically acceptable acid addition salt thereof.

17. The method of claim 15, wherein the α-adrenergic blocking agent is phenoxybenzamine or a pharmaceutically acceptable acid addition salt thereof.

* * * * *